(12) United States Patent
Eden (10) Patent No.: US 9,625,479 B1
(45) Date of Patent: Apr. 18, 2017

(54) AUTOMATED PRESERVATIVE EFFICACY TEST METHOD AND DEVICE

(71) Applicant: Neogen Corporation, Lansing, MI (US)

(72) Inventor: Gideon Eden, Ann Arbor, MI (US)

(73) Assignee: Neogen Corporation, Lansing, MI (US)

( * ) Notice: Subject to any disclaimer, the term of this patent is extended or adjusted under 35 U.S.C. 154(b) by 0 days.

(21) Appl. No.: 15/312,236

(22) PCT Filed: May 22, 2014

(86) PCT No.: PCT/US2014/039182
§ 371 (c)(1),
(2) Date: Nov. 18, 2016

(87) PCT Pub. No.: WO2015/178915
PCT Pub. Date: Nov. 26, 2015

(51) Int. Cl.
| | | |
|---|---|---|
| *C12Q 1/02* | (2006.01) | |
| *C12Q 1/06* | (2006.01) | |
| *C12Q 1/18* | (2006.01) | |
| *C12M 1/34* | (2006.01) | |
| *C12R 1/725* | (2006.01) | |
| *C12R 1/66* | (2006.01) | |
| *C12R 1/19* | (2006.01) | |
| *C12R 1/385* | (2006.01) | |
| *C12R 1/445* | (2006.01) | |
| *G01N 35/00* | (2006.01) | |

(52) U.S. Cl.
CPC ......... *G01N 35/00693* (2013.01); *C12Q 1/18* (2013.01); *G01N 2035/00702* (2013.01)

(58) Field of Classification Search
CPC ........ A61K 2039/505; A61K 2039/545; A61K 2039/55522; A61K 2039/55555; A61K 2039/55577; A61K 2039/60; A61K 2039/6056; A61K 2039/622; A61K 2039/64; A61K 39/12; A61K 39/21; C07K 14/005; C07K 2740/16122
See application file for complete search history.

(56) References Cited

FOREIGN PATENT DOCUMENTS

WO 2008015411 A1 2/2008

OTHER PUBLICATIONS

Fiorentino F.A.M. et al. The use of the challenge test to analyse preservative efficiency in non-sterile cosmetic and health products: applications and critical points. Anal. Methods, 2011, No. 3, pp. 790-798.
International Search Report and Written Opinion of the International Searching Authority for correspondence PCT Application No. PCT/US2014/039182 mailed Oct. 16, 2014.

*Primary Examiner* — Debbie K Ware
(74) *Attorney, Agent, or Firm* — Honigman Miller Schwartz and Cohn LLP; Noel E. Day; Jonathan P. O'Brien

(57) ABSTRACT

A preservative efficacy test for determining efficiency of at least one preservative material that is present in a consumable product to reduce or eliminate living microorganisms that includes challenging the preservative material with at least one microorganism derived from a pure culture by inoculating a sample of the product with a quantity of at least one challenge microorganism and allowing the microorganisms to grow for an predetermined interval after which the preservative is neutralized and a portion of the resulting sample is cultured in a testing system that includes at least one testing container, wherein the testing container contains liquid growth media and sensor means capable of monitoring microorganism growth by sensing the metabolic by-products generated by growth of microorganisms present in the liquid growth media and producing an output signal that can be measured and analyzed.

13 Claims, 4 Drawing Sheets

| ORGANISMS | INOCULUM | LOG REDUCTION | | | | | | | |
|---|---|---|---|---|---|---|---|---|---|
| | | DAY 7 | | DAY 14 | | DAY 21 | | DAY 28 | |
| | | BL | PLATE | BL | PLATE | BL | PLATE | BL | PLATE |
| E. COLI | $3.4 \times 10^5$ | <5.00 | <5.00 | <5.00 | <5.00 | <5.00 | <5.00 | <5.00 | <5.00 |
| S. AUREUS | $8.0 \times 10^7$ | <5.00 | <5.00 | <5.00 | <5.00 | <5.00 | <5.00 | <5.00 | <5.00 |
| P. AERUGINOSA | $5.6 \times 10^6$ | <5.00 | <5.00 | <5.00 | <5.00 | <5.00 | <5.00 | <5.00 | <5.00 |
| C. ALBICANS | $2.5 \times 10^5$ | <5.00 | <5.00 | <5.00 | <5.00 | <5.00 | <5.00 | <5.00 | <5.00 |
| A. BRASILIENSIS | $5.5 \times 10^6$ | 5.44 | 4.84 | <5.00 | <5.00 | <5.00 | <5.00 | <5.00 | <5.00 |

*FIG. 5*

| ORGANISMS | INOCULUM | LOG REDUCTION | | | | | | | |
|---|---|---|---|---|---|---|---|---|---|
| | | DAY 7 | | DAY 14 | | DAY 21 | | DAY 28 | |
| | | BL | PLATE | BL | PLATE | BL | PLATE | BL | PLATE |
| E. COLI | $3.4 \times 10^5$ | 5.53 | 4.69 | <5.00 | <5.00 | <5.00 | <5.00 | <5.00 | <5.00 |
| S. AUREUS | $8 \times 10^7$ | 1.12 | 1.46 | 3.14 | 2.95 | 3.58 | 2.98 | 4.45 | 3.15 |
| P. AERUGINOSA | $5.6 \times 10^6$ | <5.00 | <5.00 | <5.00 | <5.00 | <5.00 | <5.00 | <5.00 | <5.00 |
| C. ALBICANS | $2.5 \times 10^5$ | 2.42 | 1.00 | 1.28 | 0.91 | 1.46 | 1.28 | 1.84 | 1.44 |
| A. BRASILIENSIS | $5.5 \times 10^6$ | 1.54 | 1.44 | 1.36 | 1.70 | 1.38 | 1.70 | 1.74 | 1.70 |

*FIG. 6*

AUTOMATED PRESERVATIVE EFFICACY TEST METHOD AND DEVICE

The present application is a U.S. national phase of PCT Application No. PCT/US2014/039182 filed on May 22, 2014, the disclosure of which is included herein by reference in its entirety.

BACKGROUND

The present disclosure pertains to methods and devices for ascertaining the efficacy of one or more preservatives present in materials to prevent the growth of microorganisms. More particularly, the present disclosure pertains to methods and devices that can determine the efficacy and/r effectiveness of one or more preservatives present in a manufactures product in preventing or retarding the growth of microorganisms in the product.

For various manufactured products, such as cosmetic and toiletry products, a certain microbiological test Preservative Efficacy Test (PET) can be carried out to determine the efficiency of specific preservatives designed to prevent growth of microorganisms such as bacteria, yeasts and molds. Unlike regular microbiological tests (assays) that determine the presence or absence of microorganisms in a product, the PET "challenges" the product by intentionally inoculating a sample of the product with living microorganisms, and testing microorganism concentration after predetermined exposure times in order to determine whether the preservative is efficient in eliminating the microorganisms or significantly reducing their numbers.

Use of certain manufactured products contemplates repeated contact between the product and potential contamination sources. For example, many cosmetic and toiletry products such as foundations, creams, sun tan lotion, mascara and lipstick involve application techniques in which the consumer frequently touches the products in the container to obtain an application portion. This process can inadvertently introduce microorganisms to the product. In many instances, one or more preservatives are added to the product to eliminate introduced microorganisms and/or prevent or reduce microorganism proliferation. Ascertaining the efficacy of one or more of these preservatives at reducing or eliminating proliferation of undesired microorganisms that can be introduced during product use. The efficacy test is essential to verify that the product would not develop into microbiological hazard to its user.

Preservative efficacy tests (also called antimicrobial challenge tests or antimicrobial effectiveness testing) are currently performed using the traditional plate count method in which the tested product is inoculated with the microorganisms which are allowed to incubate in the product for predetermined amount of time. Thereafter the product is diluted in a neutralizing solution to eliminate the effect of the preservative in order to enable subsequent growth of the surviving microorganisms. The number of the surviving microorganisms is counted on the Petri-dish plates to determine the effect of the preservative. In the Petri-dish plate method, decimal dilutions of the neutralized inoculated product are prepared. Each decimal dilution is introduced into Petri-dish plates equipped with agar and appropriate growth media. The resulting inoculated Petri dish plates containing the agar, growth medium and an associated inoculated decimal dilution sample is are each incubated for several days enabling any surviving microorganisms to grow into colonies and which are counted.

Where the inquiry is the efficacy of the preservative after elapsed time after exposure, the efficacy test just outlined can be performed in a way that provides insight into efficacy over time. In many instances, the Petri dish method and the process just outlined is repeated for several different predetermined exposure time intervals. In certain scenarios, exposure times of one or more of the following: 7 days, 14 days, 21 days, 28 days can be employed with successful efficacy test results typically being when fewer organisms survive whenever the inoculated product is exposed to the preservative(s) as time progresses.

The Petri dish test method as outlined is also used to determine which preservative and preservative concentration provides effective protection without causing side effects to the product or to the consumer. U.S. Pharmacopeia, Chapter 51 specifies that preservative efficacy testing be conducting against various microorganisms including but not limited to the following microorganisms: *Candida albicans* (ATCC No. 10231), *Aspergillus brasiliensis* (ATCC No. 16404), *Escherichia coli* (ATCC No. 8739), *Pseudomonas aeruginosa* (ATCC No. 9027), and *Staphylococcus aureus* (ATCC No. 6538).

The traditional Petri dish efficacy test method outlined above has numerous drawbacks. The traditional Petri dish efficacy test method is a complicated multi-step method that requires extensive manual manipulation and labor. In typical cosmetic or toiletry manufacturing facilities, thousands of Petri dish plates must be individually inoculated and individual placed in incubators. Each plate has to be monitored as it incubates for its specific period of time. After incubation, the microorganism colonies that have been produced as a result of microorganism growth must be counted and the results for each Petri dish plate must be manually recorded. Both the counting operation and the recording operation are opportunities for error. Additionally, final analysis is required to verify that the reduction of organisms over time (expressed in logarithmic scale) complies with predetermined standard values specific to each combination of product, organism and progressing exposure days. Thus, it would be desirable to provide a method and device that could reduce or minimize manual operations associated with efficacy testing without compromising accuracy or efficiency. Additionally, the Petri dish method as outlined above does not effectively permit dynamic analysis of microorganism growth.

SUMMARY

Disclosed herein is a method and device for testing for the efficacy of at least one preservative present in a sample of a consumable product, the method includes the step of At time zero, inoculating the consumable product sample with an initial number of living challenge microorganisms to obtain an inoculated sample that has a first concentration of challenge microorganisms. The challenge microorganisms are obtained from at least one pure culture of the microorganisms. The preservative present in the consumable product is allowed to interact with the challenge microorganisms for an exposure time sufficient to reduce concentration of inoculated microorganisms from the first concentration of challenge microorganisms to a second concentration of challenge microorganisms. After the exposure time interval has elapsed, the interaction between the preservative and the challenge microorganisms is terminated. This termination step can include introducing at least one compound into the sample that neutralizes preservative effect of the preservative on the challenge microorganisms present in the sample to produce a neutralized sample.

The method disclosed herein also includes the step of introducing a portion of the neutralized sample into a test container, the test container containing liquid growth media and at least one sensor. The sensor is configured to monitor growth of the challenge microorganisms as by sensing metabolic byproducts generated by growth of challenge microorganisms in the liquid growth media and is capable of producing at least one output signal. The test container that contains the introduced challenge microorganisms is incubated at a temperature sufficient to promote effective microbial growth. Microbial growth is monitored as a function of time by measuring the output signal of the sensor at a plurality of time increments. The plurality of time increments may be measured as standard exposure times. The concentration of the microorganisms in the neutralized sample during incubation is determined at the plurality of time increments. The concentration of the microorganisms in the neutralized sample can be calculated using a survival calibration function that correlates the output of the sensor to the concentration of microorganisms in the neutralized sample at the time increment specified. The calibration can be derived from incubation and analysis of pure culture.

DESCRIPTION OF THE DRAWINGS

In order to further illustrate the present disclosure, reference is made to the following drawings. These drawings are to be considered illustrative and are not to be construed as limitative of the invention disclosed herein and in which.

DESCRIPTION

The method disclosed herein can be performed using a device configured to monitor and record dynamic growth of microorganisms making use of one or more sensors associated therewith. Non limiting examples devices and representative sensors are as follows. The Bactometer, manufactured by bioMerieux (bioMérieux, Inc., Hazelwood, Mo.), and the RABIT, manufactured by Don Whitley Scientific Limited (Shipley, West Yorkshire, England), utilize metal electrodes that measure the electrical impedance of the growth media as a function of time. The ESP blood culturing system, manufactured by Trek Diagnostics (TREK Diagnostic Systems, Inc. Cleveland, Ohio), measures the changing pressure in the head space of the container where the organisms are growing in the growth media and the BacT/Alert (bioMérieux, Inc., Hazelwood, Mo.), measures microbial growth using a $CO_2$ sensor. Suitable systems will be those in which the dynamic measured microorganism growth pattern can be analyzed to determine the concentration of the microorganisms in the tested sample such as in the manner generally outlined in Eden et al., "Impedance Microbiology" Research Studies Press Ltd., John Wiley & Sons Inc., 1984. Eden et al. demonstrates that the mathematical analysis in the above reference shows that the bacterial contamination level (concentration) is inversely proportional to the measured detection time (DT) which indicates the time in which the measured dynamic pattern starts to follow the exponential bacterial increase during the "logarithmic phase" of the bacterial growth.

The method disclosed herein cannot be accomplished by simply exchanging the methodology of enumerating the organisms of the Petri-dish Plate Count method with the calculated value generated by one of the automated instrumentation. The direct method fails for efficacy tests as disclosed herein as the calibration curve of the automated systems discussed above depends upon correlating detection times to bacterial concentrations and is heavily dependent upon the physical wellness of the microorganisms being measured. In the efficacy tests method as disclosed herein, health and reproduction of the microorganisms in question is substantially affected by the presence of preservative(s) integrated into the product. Any preservative inhibits or eliminates growth by altering the bacterial reproduction process. The "injured" organisms are delayed in their growth or are totally inhibited from further growth. Calibration curves produced by direct application of the devices discussed above in which Petri dishes are directly substituted from the methods associated with those devices and associated methodologies can generate erroneous efficacy test results indicating a "safe" product (sufficiently inhibiting the microorganisms) while the product may eventually become contaminated after being exposed to environmental or user contaminants The invention disclosed herein is predicated on the unexpected discovery that preservative efficacy can be ascertained in an automated manner that accurately provides results correlated with the classical efficacy tests that utilizes standard plate counts. The method as disclosed herein uses monitoring instrumentation such as that discussed previously. In addition to providing accurate results, the method disclosed herein achieves savings in cost and/or time over the standard Petri-dish plate count method in a manner that can satisfy one or more requirements promulgated by various regulatory agencies.

In the method disclosed herein, one or more test samples of a consumable material containing a preservative(s) having undergone a microbial challenge for a predetermined challenge interval is analyzed for microbial activity and growth after having the preservative(s) present in the composition neutralized.

As used herein, the term "consumable product" may be defined as any material which is administered to or used by a consumer. Of particular interest are consumable products that are configured for topical application or use including, but not limited to, toiletries such as a soaps and cleansing agents, detergents, lotions, creams, salves, emollients astringents, toners, serums. Also contemplated are materials generally classified as cosmetics, including but not limited to lipsticks, lip balms and other lip preparations, skin foundation preparations and concealers, blushes and rouges and the like. Also contemplated are various lash tinting and pigmenting agents such as mascara and the like, as well as other cosmetic products used in proximity to the eye including but not limited to eyeliners, eye shadows and the like.

In certain applications, the term "consumable product' can also include topical materials that may exhibit analgesic or therapeutic properties in particular situations. Non-limiting examples of such compositions can include materials such as salves, gels and the like as well as various solutions including but not limited to contact lens solutions and the like.

The term "preservative" as used herein can include one or more compounds or materials present in the composition that inhibit or prevent microbial growth. It is contemplated that the preservative material(s) can be a material or materials that is present in the composition and possesses or exhibits antimicrobial activity. It is also contemplated that the preservative or preservatives present in the composition can be compounds or materials that are present in the composition specifically for antimicrobial activity or function.

In the method disclosed herein, the preservative(s) present in composition are subjected to challenge by one or more challenge microorganisms for a suitable challenge interval. The challenge interval can be one sufficient to exhaust or deplete preservative action in at least a portion of the exposure events and to provide relevant performance data. In many, instances, the challenge interval will be at least one day, with intervals of seven days, fourteen days, twenty-one days and/or twenty-eight days being typically employed. It is understood that that other intervals can be specified as desired or required. It is contemplated that, in certain applications, multiple product samples can be inoculated in order to provide performance data over multiple challenge intervals. It is also contemplated that various multiple product samples can be exposed to one or more challenge microorganisms with the challenge microorganisms being either a single individual organism type or a combination of organism types as desired or required.

The challenge microorganism can be one that one or more microorganism strains of yeasts, molds, bacteria or the like that can infect the product composition in question. Non limiting examples of such microorganisms include one or more of the following: *Candida albicans* (ATCC No. 10231), *Aspergillus brasiliensis* (ATCC No. 16404), *Escherichia coli* (ATCC No. 8739), *Pseudomonas aeruginosa* (ATCC No. 9027), and *Staphylococcus aureus* (ATCC No. 6538). It is contemplated that the method disclosed herein can be employed with these challenge microorganisms where desired or required.

In one embodiment of the method as disclosed herein a portion of the product composition to be assayed, is transferred into one or more sterile containers. The size of the product portion used can be that sufficient to provide substrate for the challenge test. In certain embodiments, the portion can be between 1 and 100 grams, with portions between 5 and 30 grams being typical in certain applications. Where analysis under multiple challenge intervals is desired, multiple portions of the product composition can be transferred to multiple corresponding containers. For example, a 50 gram portion of the product composition to be studied, may be transferred in 10 gram portions to five individual sterile containers.

The containers thus prepared containing the measured portion of the product composition can be inoculated with a measured portion of liquefied pure culture of the challenge microorganism under study. As used herein the term pure culture is generally defined as a specifically grown and cultured strain of the microorganism of interest at a known initial microbial concentration. This can be obtained by any suitable method as by suitable culturing and harvest of a known initial colony forming unit and dilution to a known concentration.

The inoculant and product sample are mixed in a manner that provides intimate contact between the product and microorganism in the inoculant. The resulting admixture d permitted to remain undisturbed for the desired exposure interval, with exposure intervals of seven, fourteen, twenty-one and twenty four days being typical in certain situations. The samples can be maintained at a suitable temperature during this interval. In certain situations, it is contemplated that the temperature during the exposure interval can be one that would mimic growth conditions typically encountered with the associated product composition during expected use conditions. Thus the temperature during exposure interval can be one that approximates standard use conditions of the product. Alternately, temperature can be one that mimics extremes as necessary.

Once the predetermined exposure interval has elapsed, the interaction between preservative in the composition and the challenge microorganisms can be terminated in each of the test containers. This can be accomplished by introducing a neutralizing agent capable of eliminating the effect of the preservative on the challenge microorganisms into the composition with suitable mixing. The neutralizing agent will be one that selectively eliminates the preservative effect without compromising activity of any challenge microorganisms that may remain in the test sample. Suitable neutralizing agents include those typically employed in Petri dish test methodology. Where desired or required, the neutralizing material can be present in a solution at a known concentration such that a measured quantity of neutralizing agent solution can be introduced into each respective test container.

Once the action of the preservative has been neutralized, a portion of the resulting test sample mixture can be introduced into a test container or vial that is configured with liquid growth media and at least one sensor capable of monitoring microorganism growth. Monitoring microorganism growth can be accomplished by various methods. In certain embodiments disclosed herein, microorganism growth can be determined by sensing the increase of metabolic by-products generated by the microorganism growth.

Test containers or vials employed in the method as disclosed herein can include a portion of liquid growth medium that contains suitable nutrients capable of supporting efficient growth of microorganisms that may be present in the test sample. Non-limiting examples of specific and non-specific liquid growth media that can be used include Triptic Soy Broth, Plate Count Broth (Difco, Becton Dickenson and Company, Sparks, Md., USA), or CM-Coliform Medium (bioMerieux, Hazelwood, Mo., USA). It is also considered to be within the purview of the present invention to utilize various types of selective media for the detection of molds and yeast, or selected groups of organisms, such as Staphylococcus, *E. coli*, or lactic acid bacteria can be used where desired or required.

In certain embodiments, the sensor employed in the test container or vial can be one that produces a change in light transmittance characteristics in at least a portion of the test container or vial. The sensor can include, but is not limited to, various indicator reagents or dyes. The location of the indicator reagent or dye in the container can vary depending on the device employed. In certain configurations, the indicator reagent or dye can be a material that is dispersed throughout all or part of the liquid growth medium. It is also contemplated that the indicator reagent or dye can be entrained in suitable media at a defined location in the container.

Non-limiting examples of indicator reagents that can be employed in the various desired include materials such as Thymolphtalein, Bromothymol blue and Xylenol Blue. Other examples of indicators that can be used in the visible light range include pH indicators, such as Bromocresol Purple, Chlorophenol Red, Brothymol blue (Sigma-Aldrich, St. Louis, Mo., USA), and reduction indicators, such as Methylen Blue, Resazurin and Tetrazolium (Sigma-Aldrich, St. Louis, Mo., USA). Fluorescence compounds, with changes of properties in the UV range, can be used as indicator substrates, such as a variety of Umbelliferones and Coumarins. For example, 4-methyl-umbelliferyl-3-D-glucuronide (MUG) (Sigma-Aldrich, St. Louis, Mo., USA), can be used in conjunction with selective media to detect *E. coli*. 4-methyl-urnbelliferyl phosphate (MUP) (Sigma-Aldrich, St. Louis, Mo., USA) can be used as many organisms metabolize this compound to create fluorescence. PYR (pyroglutamyl aminopeptdase reaction) is useful in the identification of group A streptococci, and L-pyroglutammyl-7-amino-4-methylcoumarin can be used as an indicator of PYR activity. It is contemplated that various other chromomeric and enzymatic compounds that can be utilized as desired or required.

Test container s or vials can have any suitable configuration. In certain embodiments, the test vial can be a plastic vial that has a least one region that is transparent to light. The light may be in the visible range and at least a fraction of the long ultraviolet range. For example, polycarbonate can be used which is transparent to the entire visible spectrum and to long ultraviolet radiation above 350 nanometers.

Figure 1:
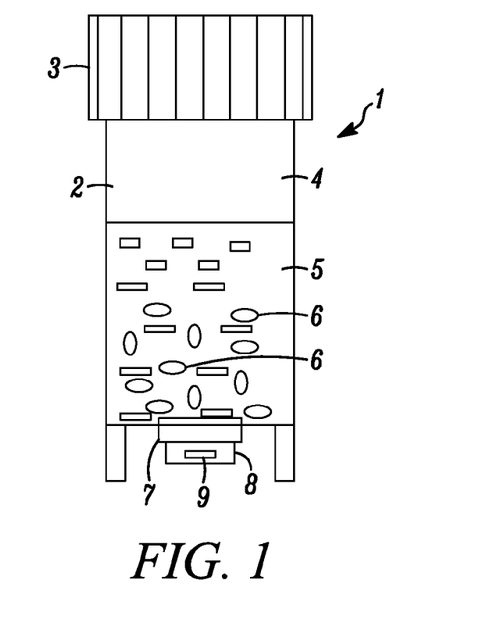
FIG. 1 is a side elevational view of an embodiment of a device that can be employed in the method as disclosed herein.
Figure 2:
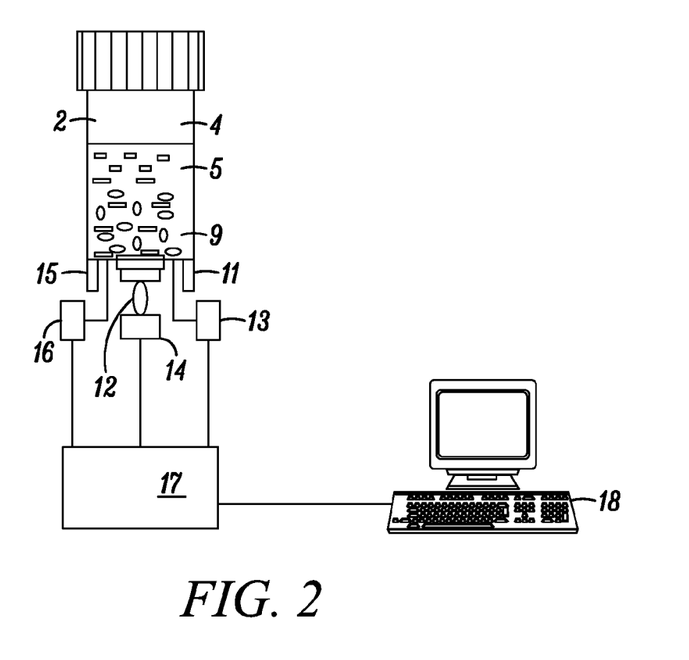
FIG. 2 is a diagram of an experimental setup of an automated reader associated with the device shown in FIG. 1

In the non-limiting example depicted, a container or vial 2 such as that disclosed in FIG. 1 can be used with the device depicted in FIG. 2 and can be sealed with a cap 3 if desired or required. In certain applications, the cap 2 can be made of polycarbonate as well. In certain applications, it is contemplated that both the container or vial 2 and the cap 3 can be composed of a material that can be thermally sterilized at 121° C., and polycarbonate can endure such temperature.

In certain embodiments, the container or vial 2 can have a container bottom that includes at least one window such as a rectangular window 8. The window 8 has two parallel opposing surfaces (one surface is shown in the FIG. 3) and should be transparent to light, as indicated above. The internal volume of the container or vial 2 consists of a head space 4, growth zone 5, and detection zone 9. As shown in the FIG. 1 a liquid mixture of reagents can be introduced into the vial 2 to occupy at least zone 5. The detection zone 9 can be either solid, liquid or semi-solid as desired or required.

One suitable device configuration is depicted in FIG. 2 where the container or vial 2 is combined with an optical instrumentation device to detect changes in light transmittance and/or absorbance that is associated with microbial growth. The instrumentation device can be configured to receive multiple containers of vials 2.

The instrumentation device can be configured such that one or more multiple light source units can be associated with each respective container or vial 2. For example, in the embodiment depicted in FIG. 2, there are two light source units such as a visible light source 11 and an ultraviolet light source 12. Visible light source units 11 can be incandescent light bulbs, light-emitting diodes, gas discharge tubes or the like. The visible light source 11 and the ultraviolet source 12 can receive their energy and be controlled by suitable mechanisms such as controllers 13 and 14, respectively.

The instrumentation device can include one or more photodetectors that are associated with a respective container or vial 2. In the embodiment depicted in FIG. 2, single photo-detector 15 is associated with a respective container or vial 2. The photodetector 15 can be used to detect the energy generated by the interaction of the energy from the light sources with the indicator substrate in the detection zone 9. The photo-detector 15 can either be a photo diode, photo transistor, photon multiplying tube (PMT) or any other light-sensitive device. In the device depicted, an amplifier 16 amplifies the analog signal detected by the photo-detector 15. An electronic processor 17 activates the light sources 11 and 12 by sequentially switching on the controllers 13 and 14, and processes the resulting signal which can be transmitted to a suitable CPU or other device as desired or required.

The liquid mixture of reagents can be a mixture of growth media. The liquid phase in the container is a mixture of growth media and at least one indicator substrate. The growth media enables efficient growth of microorganisms originating from the test sample. Several specific and non-specific media can be used, such as mPCB (Difco, Becton Dickenson and Company, Sparks, Md., USA) with Bromocresol Purple as an indicator for total aerobic plate count, or CM-Coliform Medium (bioMerieux, Hazelwood, Mo., USA). Selective media for the detection of molds and yeast, or selected groups of organisms, such as *Staphylococcus, E. coli*, or lactic acid bacteria can be used In the method disclosed herein, the test vial(s) containing the sample portion with neutralized preservative are incubated at a temperature that promotes growth of the challenge microorganism that have been introduced to the product sample prior to preservative neutralization. Microorganism growth is monitored at specific intervals and is recorded as a function of time by measuring the output signal of the sensor means at specific time increments and determining the detection time from the generated time pattern. In certain embodiments of the method disclosed herein output measurement can measured at specific intervals between 4 and 10 minutes with intervals of 6 minutes being employed in certain embodiments. Detection time can be determined from the generated measurements.

The concentration of microorganisms in the respective test sample can be determined by applying a primary calibration curve correlating the detection time to microorganism concentration as determined by the plate count method at the predetermined exposure time. The reduction (or increase) in microorganisms in the sample can be obtained by calculating the concentration of the microorganisms at the specific exposure time(s) relative to the concentration of microorganism(s) in a reference mixture that is obtained by mixing the neutralizing agent after a reduced exposure time (typically several hours) following the sample inoculation and by applying a secondary calibration curve correlating the generated detection time of pure culture of the microorganisms to their concentration as determined by the plate count method.

The present method may also include the step of determining effectiveness of the preservative in preventing or reducing microorganism growth. This can be accomplished by comparing the reduction of each of the microorganisms at the predetermined exposure times to the greed upon standards such as those described in U.S. PHARMACOPEIA Chapter 51.

The method disclosed herein can be repeated for various exposure times such as those currently employed in the Petri dish plate count method. The process can be automated by any of the newly developed sensor systems capable of monitoring the generation of metabolic by-products in liquid media, by utilizing various typed of metabolic sensors as such as optical sensors, impedance based sensors and gas sensors. For example, an optical sensor can measure the turbidity in the growth media measured from the projected light scattering off of the organism cells. Another example is a dye indicator (such as pH indicator such as Brome-Cresol-Purple or enzymatic indicator such as fluorescing MUG) mixed with the liquid growth media. In such cases, an optical sensor can measure one or more changes in optical indicators whether in the visible range, in UV, IR or as fluorescence. Another example of a sensor system that can be employed in the method as presently disclosed is a $CO_2$ sensor embedded in the container adjacent to the liquid media where the microorganisms grow, monitoring the generation of $CO_2$ by the metabolizing organisms. The common denominator of these sensors is their capability to generate time patterns by saving the sensor's output at specific time intervals.

Figure 3:
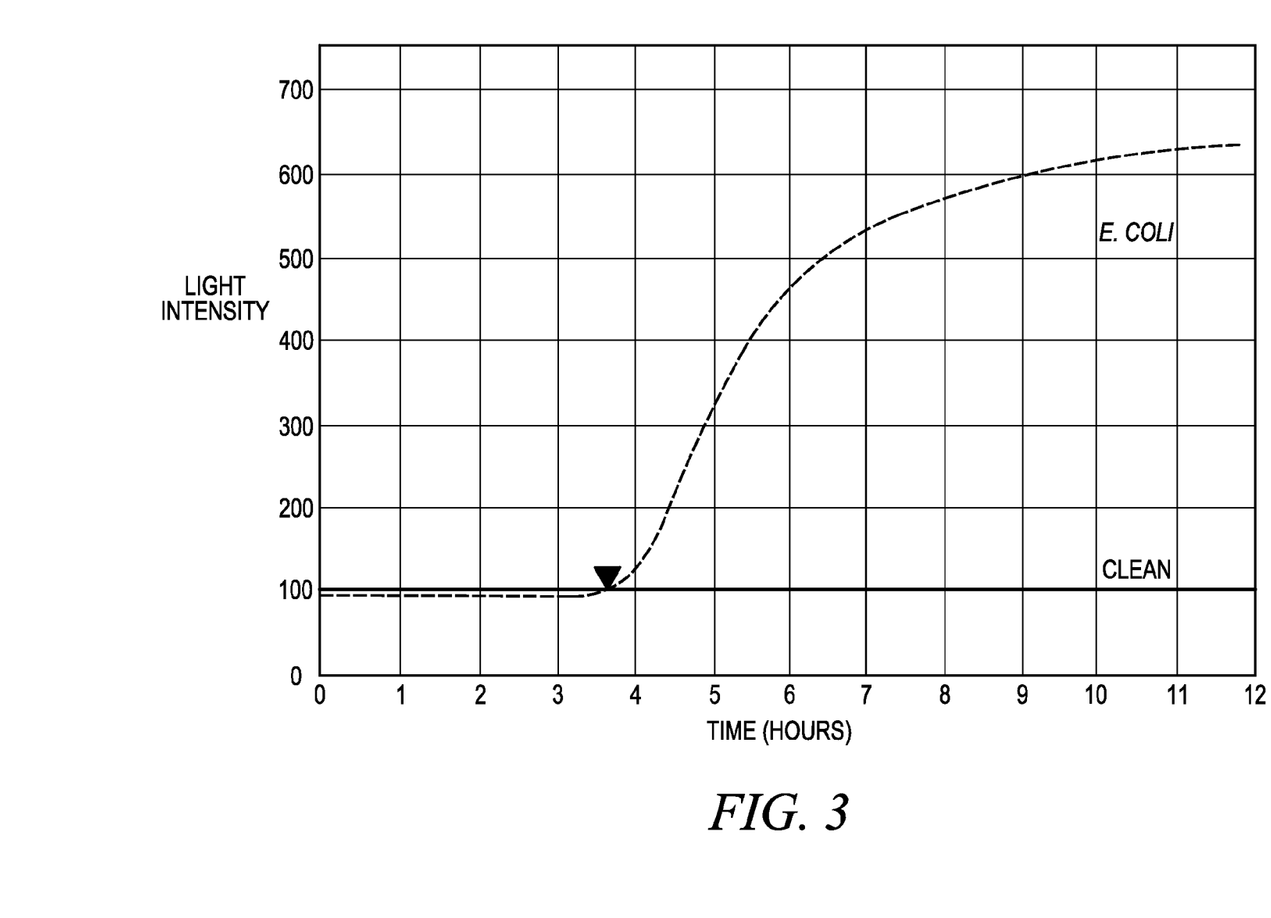
FIG. 3 is a graphic depiction of a representative growth curve for e Coli and one for a clean sample as a function of light intensity vs. time according to an embodiment of the method as disclosed herein.

By way of example, FIG. 3 shows two dynamic patterns of an optical based sensor for a sterile sample and for a contaminated sample with *E. coli*. If there are no microorganisms in the sample the pattern is virtually flat. A contaminated sample is characterized by a flat initial portion followed by an accelerating portion which follows the logarithmic phase of the microorganisms' growth (the phase after the Lag Period in which the organisms grow exponentially). The time of the deflection point between the flat and the accelerating portions of the pattern is defined as the detection time (DT). In FIG. 3, the detection time is determined to be 3.7 hours marked by the black triangle.

A mathematical analysis of the relationship between the DT and the bacterial concentration in the sample has been developed in Impedance Microbiology by Eden et al, Research Studies Press Ltd., John Wiley & Sons Inc. 1984. This analysis enables the generation of calibration curves for various applications for different products/microorganisms combinations. More specifically the calibration curve is a line formula with at least 2 coefficients A and B in the form similar to $$\log(CFU) = A - B*DT$$

where DT is the detection time and CFU is the Colony Forming Units developed and counted in a standard corresponding Petri-dish plate which indicates the concentration of the organisms in the sample. The term log is the mathematical logarithm function.

Incubation and microorganism growth can be accomplished by any suitable means. In specific embodiments disclosed herein, it is contemplated that incubation and microorganism growth can be supported and monitored using a monitoring system such as available in the BioLumix system To further illustrate the present disclosure attention is directed to the following examples which are presented to illustrate the present disclosure and are not considereared limitative.

EXAMPLE 1

Generation of Calibration Curves—
*Pseudomonas aeruginosa* is inoculated into several cream products with similar preservative systems. The innoulated cream products were allowed to sit undisturbed for various exposure intervals after which the various samples were neutralized and respective portions of each neutralized sample were introduced into tests vials conaining growth media and incubated in a BioLumix-32 optical instrument. The detection times were obtained by utilizing the BioLumix-32 optical instrument and its test vials (BioLumix Inc. Ann Arbor Mich. USA).

Figure 4:
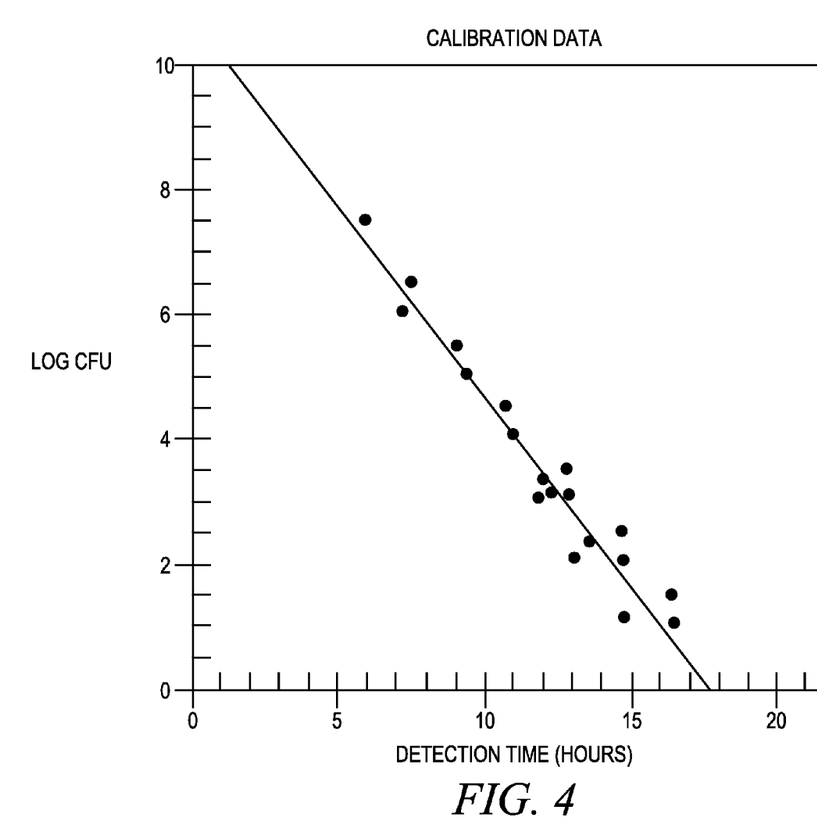
FIG. 4 of graphic depiction of a representative calibration curve for p Aeruginosa inoculated cream product expressed as the logarithmic function of colony forming units of microorganisms vs. detection time according to an embodiment disclosed herein.

FIG. 4 shows the calibration curves obtained with *Pseudomonas aeruginosa* inoculated into several cream products with similar preservative systems. As can be seen all results fit on a single calibration curve. The line equation obtained was.

$$\text{Log cfu/gram} = 10.88 - 0.618*DT$$

The correlation coefficient (R) was 0.97.

The line equations of each calibration curve for each microorganism was embedded into the optical instrument software. The software calculated the log reduction after the 7, 14, 21, and 28 days, for each organism.

Mixtures of microorganisms can also be used to generate calibration curves provided that all the organisms in the mixture have similar generation times to fit on a single calibration curve. For purposes of this example, a mixture of Fermentative Gram Negative Bacilli, including *Klebsiella pneumoniae*, ATCC #13883, *Escherichia coli* ATC'C#8739, and *Enterobacter gergoviae*, ATCC #33028 were used.

EXAMPLE 2

Evaluation of eye drop formulation with and without benzalkonium chloride (BAK)—Benzalkonium chloride (BAK) is generally regarded as an effective agent for preventing bacterial contamination of glaucoma eye-drops. However, its advantages and disadvantages are under scrutiny for possible effects on medical and surgical management. To evaluate the correlation of the newly developed method, two formulas of eye-drops were used, one contained BAK and the second without the BAK preservative. Using the BioLumix-32 instrument the results for samples of eyed drops containing preservative against *E. coli, S. aureus, P. aeruinosa, C albicans, A. brasiliensis* were obtained and are set forth in the Table in FIG. 5. Eye drops whithout BAK were also tested in the same manner. The results are summarized in the table set forth in FIG. 6.

Figure 5:
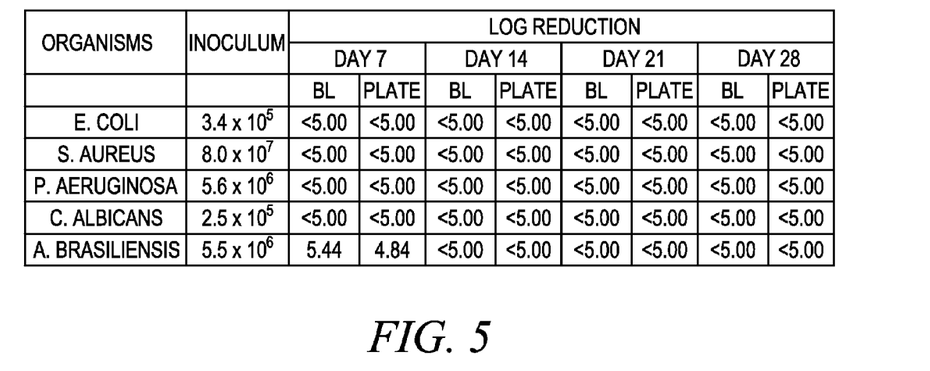
FIG. 5 is a table depicting effectiveness of benzalkonium chloride (BAK) in an eyedrop formulation against various organisms.
Figure 6:
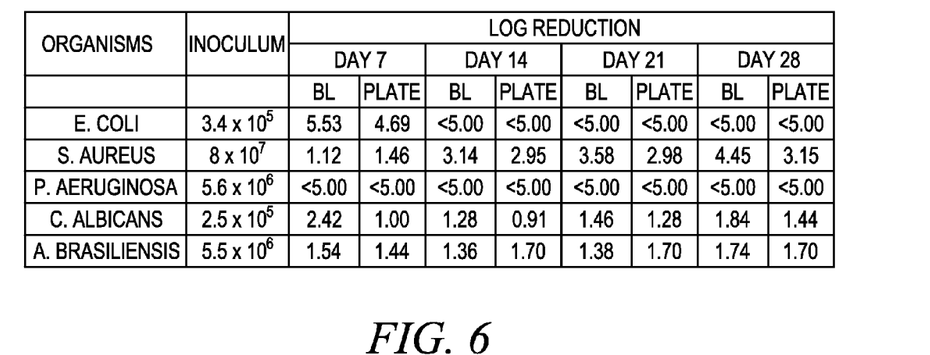
FIG. 6 is a is a table depicting effectiveness of the eyedrop formulation employed in FIG. 5 without benzalkonium chloride (BAK) against various organisms

As illustrated in FIG. 5, the eye-drops with BAK were reduced at least 5.00 logs of each of the organisms, with the exception of *A. brasiliensis*, after 7 days and no growth was observed thereafter in up to 28 days. Both the plate count method and the method as disclosed herein showed the same trends. *A. brasiliensis* concentration was reduced by around 5 logs in 7 days and was totally inhibited thereafter, as determined by both methods The eye-drops without BAK demonstrated a 5 log concentration reduction by both methods only for *P. aeruginosa*. It took 14 days to inhibit the *E. coli*. In the remaining organisms, only partial and slow reduction of the organisms were obtained. The same trends are seen by the standard USP method and the new method. The new method uses a single vial instead of several plates, dilution blanks and pipette tips. Upon completion of the PET tests using the optical instrument, a certificate of analysis with a succinct report of the microbiological properties of each product was generated.

While the invention has been described in connection with what is presently considered to be the most practical and preferred embodiments, it is understood that the invention is not limited to the disclosed embodiments, but is intended to cover various modifications and equivalent arrangements included within the spirit and scope of the claims. The claims are to be accorded the broadest possible interpretation so as to encompass all such modifications and equivalent structures and instructions as permitted under the law.

What is claimed is:

1. A preservative efficacy testing method for testing efficiency of at least one preservative material present in a consumable product to reduce or eliminate living microorganisms, the testing method comprising the steps of:
   (a) inoculating a sample of the consumable product at time zero with initial number of living microorganisms, the living microorganisms derived from at least one pure culture of the respective living microorganisms to produce an inoculated sample, wherein the living microorganisms in the inoculated sample are present as a volumetric portion of the respective pure culture;
   (b) allowing the at least one preservative material in the consumable product to interact with the inoculated microorganisms in the inoculated sample for a predetermined standard exposure time in order to reduce concentration of living microorganisms in the inoculated sample;
   (c) terminating interaction between the at least one preservative material and the living microorganisms at a predetermined standard exposure time, wherein the interaction termination step occurs by mixing the inoculated sample with at least one neutralizing agent, wherein the neutralizing agent is at least one compound that is capable of eliminating the microorganism reduction effect of the preservative material to produce a neutralized sample;
   (d) introducing a portion of the neutralized sample into a testing system, the testing system including at least one testing container, wherein the testing container contains liquid growth media and sensor means capable of monitoring microorganism growth by sensing the metabolic by-products generated by growth of microorganisms present in the liquid growth media and producing an output signal;
   (e) incubating the at least one testing container at a temperature sufficient to effect growth of the microorganisms and monitoring microorganism growth as a function of time, wherein microorganism growth monitoring occurs by measuring the output signal of the sensor means at specific time increments to yield a microorganism growth value curve;
   (f) determining concentration of the microorganisms in the neutralized sample at the predetermined standard exposure time based on the output signal of the sensor means, determination of concentration determination occurring by applying a survival calibration function to the concentration of the surviving microorganisms in the neutralized sample, wherein the survival calibration function correlates the output of the sensor means with concentration of the surviving microorganisms;
   (g) at time zero introducing a portion of the at least one pure culture from which the living microorganisms are derived into at least one container in the testing system;
   (h) incubating the at least one testing container containing living microorganisms from the at least one pure culture at a temperature sufficient to effect growth of the microorganisms and monitoring microorganism growth as a function of time, wherein microorganism growth monitoring occurs by measuring the output signal of the sensor means at specific time increments;
   (i) determining microorganism concentration in the pure culture from output of the sensor means, the determination step occurring by applying a pure-culture-calibration function to the concentration of the microorganisms in the pure culture, wherein the pure-culture calibration function correlates the output of the sensor means with concentration of the pure-culture microorganisms;
   (j) calculating concentration of the microorganisms in the inoculated sample immediately after the inoculation step by calculating the volumetric proportion of the pure culture in the inoculated sample of the consumable product to yield a reference-microorganisms concentration value;
   (k) calculating reduction in the concentration of the microorganisms in the inoculated sample at the predetermined standard exposure time relative to the reference-microorganisms-concentration value in the reference sample;
   (l) determining whether the preservative material is efficient in reducing the concentration of the microorganisms in the consumable product by comparing said calculated reduction at said exposure time to a predetermined reduction standard for identical standard exposure time.

2. The method of claim 1 wherein the pre-determined standard exposure time is chosen from a group consisting of 1, 7, 14, 21 and 28 days.

3. The method of claim 1 wherein the living microorganisms is chosen from a group that includes at least one of the following strains: *Candida albicans, Aspergillus brasiliensis, Escherichia coli, Pseudomonas aeruginosa, Staphylococcus aureus.*

4. The method of claim 1 wherein the sensor means is at least one of the following: an electronic optical sensor measuring turbidity of the microorganisms in the liquid media, an optical sensor embedded in the testing container measuring colorimetric changes of an embedded dye indicator, an optical sensor measuring fluorescence variations in an embedded fluorometric substrate, an ATP luminescence sensor, a gas sensor measuring the consumption of oxygen by the microorganisms, a gas sensor measuring the generation of carbon dioxide by the microorganisms, a pressure sensor measuring the generation or consumption of gases by the microorganisms, electrodes embedded in the liquid media measuring electrical properties of the liquid media, an immunoassay-based sensor, a DNA-based sensor.

5. The method of claim 1 wherein the survival calibration function and the pure-culture-calibration function are line equations each comprising at least two sets of coefficients A and B in the form similar to $$\log(CFU)=A-B*DT$$

wherein the term DT is the detection time determined as the time when the output of the sensor means starts following the pattern of the logarithmic growth phase of the microorganisms growing in the liquid media;
   wherein A and B are experimentally determined by correlating at least two Detection Time values to the corresponding microorganism concentrations as determined by the standard plate counts method; and
   wherein the term log denotes the mathematical logarithmic function.

6. The method for testing the efficiency of a preservative material present in a consumable product to reduce or eliminate living microorganisms, comprising multiple repetitions of the steps in claim 1 applied to several predetermined standard exposure times, and calculating the corresponding reductions in the concentration of the living microorganisms in the corresponding inoculated samples.

7. The method for testing the efficiency of a preservative in a consumable product to reduce or eliminate living microorganisms, comprising multiple repetitions of the steps in claim 1 applied with different pure cultures of different strains of microorganisms.

8. The method for testing the efficiency of a preservative in a consumable product to reduce or eliminate living microorganisms, comprising multiple repetitions of the steps in claim 1 applied with mixtures of different pure cultures of different strains of microorganisms.

9. The method of claim 2 wherein the living microorganisms is chosen from a group that includes at least one of the following strains: *Candida albicans, Aspergillus brasiliensis, Escherichia coli, Pseudomonas aeruginosa, Staphylococcus aureus.*

10. The method for testing the efficiency of a preservative material present in a consumable product to reduce or eliminate living microorganisms, comprising multiple repetitions of the steps in claim 2 applied to several predetermined standard exposure times, and calculating the corresponding reductions in the concentration of the living microorganisms in the corresponding inoculated samples.

11. The method for testing the efficiency of a preservative in a consumable product to reduce or eliminate living microorganisms, comprising multiple repetitions of the steps in claim 2 applied with different pure cultures of different strains of microorganisms.

12. The method for testing the efficiency of a preservative in a consumable product to reduce or eliminate living microorganisms, comprising multiple repetitions of the steps in claim 2 applied with mixtures of different pure cultures of different strains of microorganisms.

13. A device for assessing the efficiency of a preservative present in a consumable product to reduce or eliminate living microorganisms, comprising a central processing unit (CPU) embedding the survival calibration function and the pure-culture-calibration function of claim 1 to determine the concentration of the surviving microorganisms in the neutralized sample and the concentration of the microorganisms in the pure culture respectively.

* * * * *